(12) United States Patent
Holladay (10) Patent No.: US 7,049,446 B2
(45) Date of Patent: May 23, 2006

(54) PROCESS FOR CHEMICAL REACTION OF AMINO ACIDS AND AMIDES YIELDING SELECTIVE CONVERSION PRODUCTS

(75) Inventor: Jonathan E. Holladay, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 56 days.

(21) Appl. No.: 10/841,687

(22) Filed: May 6, 2004

(65) Prior Publication Data

US 2004/0225133 A1    Nov. 11, 2004

Related U.S. Application Data

(60) Provisional application No. 60/468,614, filed on May 6, 2003.

(51) Int. Cl.
*C07D 207/04* (2006.01)
*C07C 215/00* (2006.01)
*C07C 27/04* (2006.01)

(52) U.S. Cl. .................. 548/570; 564/503; 564/355; 568/885

(58) Field of Classification Search ............... 548/570; 564/503, 355; 568/885
See application file for complete search history.

(56) References Cited

U.S. PATENT DOCUMENTS

| 5,536,879 A | 7/1996 | Antons et al. |
| 5,731,479 A | 3/1998 | Antons |
| 6,310,254 B1 * | 10/2001 | Antons et al. ............... 564/503 |

OTHER PUBLICATIONS

Adkins et al., J. Am. Chem. Society., 1934, 56, p. 689.
Adkins et al., J. Am. Chem. Society., 1938, 60, p. 402.
Carnahan et al., J. Am. Chem. Society., 1955, 77, p. 3766.
Miller et al., Organic Letters, 2003 5(4), pp. 527–530.
Broadbent et al., J. Org. Chem., 1959, 24, p. 1847.

* cited by examiner

*Primary Examiner*—Kamal A. Saeed
*Assistant Examiner*—Susannah L. Chung
(74) *Attorney, Agent, or Firm*—James D. Matheson

(57) ABSTRACT

The invention relates to processes for converting amino acids and amides to desirable conversion products including pyrrolidines, pyrrolidinones, and other N-substituted products. L-glutamic acid and L-pyroglutamic acid provide general reaction pathways to numerous and valuable selective conversion products with varied potential industrial uses.

23 Claims, 6 Drawing Sheets

PROCESS FOR CHEMICAL REACTION OF AMINO ACIDS AND AMIDES YIELDING SELECTIVE CONVERSION PRODUCTS

This application claims priority to provisional application No. 60/468,614 filed May 6, 2003 now abandoned, which contents are incorporated by reference as if fully rewritten herein.

This invention was made with Government support under Contract DE-AC0676RLO-1830 awarded by the U.S. Department of Energy. The Government has certain rights in the invention.

BACKGROUND OF THE INVENTION (1) Field of the Invention

The present invention relates generally to reaction pathways and processes for chemical conversion of amino acids and amides to selective conversion products. More particularly, the present invention relates to selective chemical reaction of L-glutamic acid [CAS no. 56-86-0] and L-pyroglutamic acid [CAS no. 98-79-3] and other related compounds yielding intermediate and end-use products at greater-than-expected yields. Such compounds find applications in such commercial products as solvents, plastics, epoxies, coatings, and urethanes.

(2) Background

Figure 1A:
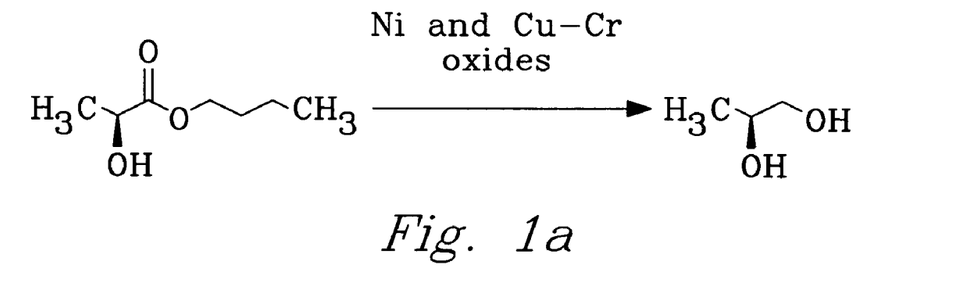
FIGS. 1a–1c present teaching in the prior art to metal catalyzed hydrogenation reactions.
Figure 1B:
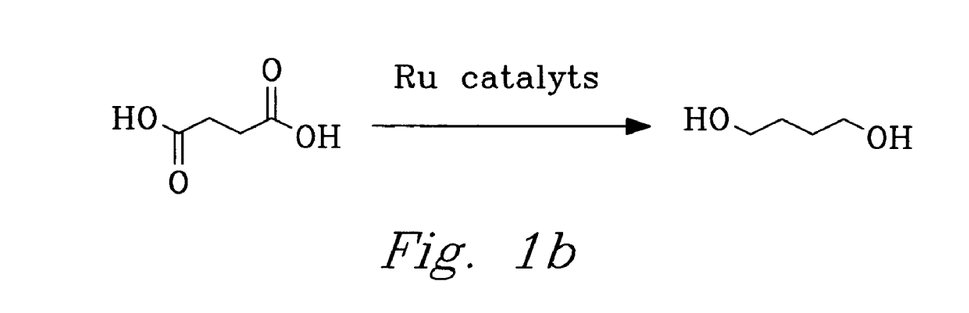
Figure 1C:
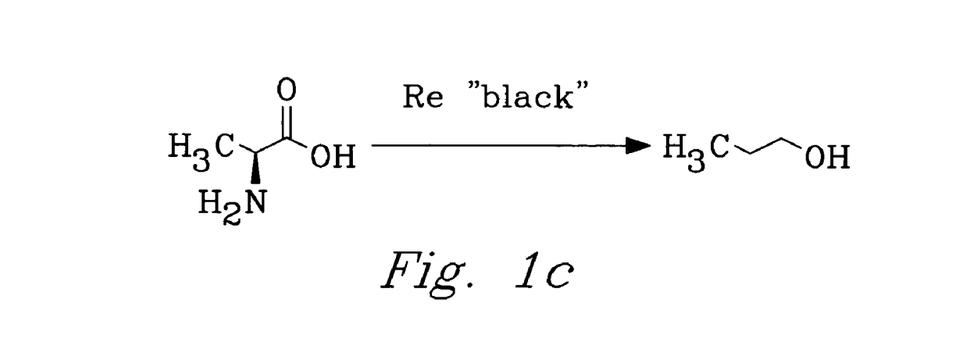

Metal catalyzed hydrogenation reactions in the presence of acid at low pH have been shown in several early seminal publications. FIGS. 1a–1c illustrate conversion products stemming from the pioneering work of Adkins et al. (FIG. 1a), Carnahan et al. (FIG. 1b), and Broadbent et al. (FIG. 1c). Adkins et al. (*J. Am. Chem. Soc.*, 1934, 56, p. 689) used various transition metal oxides including those of nickel, copper, and chromium to reduce carboxylic acid esters to alcohols, including, as illustrated in FIG. 1a, conversion of butyl lactate to propylene glycol. Adkins et al. (*J. Am. Chem. Soc.*, 1938, 60, p. 402) later reported reduction of amides via hydrogenation reactions in which Cu—Cr oxide catalysts were used and reduction of a lactam carbonyl using a ruthenium catalyst. Results showed reduction of amides in water typically yields amines whereas reduction of lactams yields alcohols. Carnahan et al. (*J. Am. Chem. Soc.*, 1955, 77, p. 3766) demonstrated conversion of di-carboxylic acids to diols using a ruthenium metal catalyst, as illustrated in FIG. 1b. Broadbent et al. (*J. Am. Chem. Soc.*, 1959, 24, p. 1847) later used a rhenium "black" catalyst to deaminate and hydrogenate amino acids yielding aliphatic alcohols, as illustrated in FIG. 1c.

The stereo-specific hydrogenation of amino acids has also been reported in the prior art. U.S. Pat. Nos. (5,536,879), (5,731,479), and (6,310,254) assigned to Bayer disclose hydrogenation reactions involving amino acids requiring conditions of low solution pH, extremely high ruthenium oxide/rhenium oxide ($RuO_2/Re_2O_7$) catalyst loading, large hydrogen partial pressures (3000 psi), prolonged reaction times (e.g., 8 hours), and reaction temperatures near 70° C. Product yields for the conversion products glutamic acid and pyroglutamic acid were reported to be 58% and 65%, respectively, with an enantiomeric excess approaching 98.3%.

In more recent work by Miller et al. [*Organic Letters*, 2003, 5(4), p. 527], the conversion of alanine to desired products stresses the importance of performing hydrogenations at low pH such that the amino acid is in protonated form rather than carboxylate form. Miller et al. further disclose conditions of a 5% ruthenium metal catalyst and partial hydrogen pressures of 6.9 Mpa (1000 psi). Under neutral pH conditions the zwitterion is not reported to reduce to a functional moiety of interest and favorable reduction of amino acids is minimal.

In general, the prior art teaches that reactions to reduce amino acids require a low solution pH in conjunction with high catalyst loading, prolonged reaction times, and large hydrogen partial pressures. The present invention demonstrates novel pathways and conditions not taught or suggested in the literature for converting amino acids, amides, and substituted amides to highly desirable intermediate and end-use products at high selectivity and high yield.

SUMMARY OF THE INVENTION

The present invention generally provides processes for converting amines and amides to highly desirable intermediate and end-use products at both high selectivity and high yield. In particular, the present invention relates to selective chemical reaction of L-glutamic acid and L-pyroglutamic acid (5-oxopyrrolidine-2-carboxylic acid) forming numerous conversion products.

In one embodiment, the conversion product is selected from amines, cyclic amines, alcohols, or combinations thereof. In another embodiment, the conversion product is prolinol. In yet another embodiment, the conversion product contains a ring having a carbon number in the range from about 4 to about 7.

The processes of the present invention generally comprise the steps: a) providing a starting material in a solvent; b) optionally reacting said material thereby yielding at least one amide; and, c) reducing at least one amide in the presence of a reduction catalyst thereby yielding at least one amine at high yield. Starting materials are preferably selected from amides, lactams including but not limited to pyrrolidinones, 2-pyrrolidinone and N-methylpyrrolidinone being representative but not exclusive, and amino acids, glutamic acid being representative but not exclusive.

In one embodiment, the starting material comprises a member selected from: amino acids, amides, lactams, pyrrolidinones, or combinations thereof. In another embodiment the starting material comprises a member selected from glutamic acid, pyrrolidinones, 2-pyrrolidinone, N-methyl pyrrolidinone, pyroglutamic acid, pyroglutaminol, or combinations thereof. In yet another embodiment, the starting material comprises amino acids selected from lysine, aspartic acid, asparagine, glutamine, glutamic acid, arginine, pyroglutamic acid, ornithine, or combinations thereof. In still yet another embodiment, the starting material comprises a carbon number in the range from about 1 to about 20. The term amino acid as used herein refers to moieties having an amino group (i.e., $NH_2$) and an acid group (i.e., COOH). The term "reacting" as used herein refers to reactions including, but not limited to, cyclization, condensation, hydrogenation, reduction, decarboxylation, deamination, and combinations thereof. Conditions are specified that result in high yields under selected conditions of elevated temperature, controlled solution pH, and precious-metal catalyst combinations.

It is an object of the present invention to show conversion of amino acids at enhanced conversion rates in the presence of catalysts, e.g., precious metal catalysts on supports.

It is further an object of the present invention to show conversion of carboxylic acid functional groups of glutamic acid and other amino acids to yield desirable intermediate and end-use products.

It is still further an object of the present invention to show it may be unexpectedly undesirable to convert certain amino acid moieties under conditions of low pH.

BRIEF DESCRIPTION OF THE DRAWINGS

A more complete appreciation of the invention will be readily obtained by reference to the following description of the accompanying drawings in which like numerals in different figures represent the same structures or elements.

DETAILED DESCRIPTION OF THE INVENTION

While the present invention is described herein with reference to the preferred embodiments thereof, it should be understood that the invention is not limited thereto, and various alternatives in form and detail may be made therein without departing from the spirit and scope of the invention. In particular, those skilled in the art will appreciate that the methods set forth herein for producing specific moieties or other similar chemical products or intermediates can be derived with high specificity, high selectivity, and/or high yield.

The term "yield" as used herein refers to a quantity formed of product of interest. Yield is calculated as conversion multiplied by selectivity, i.e., [Y]ield=[C]onversion× [S]electivity, where "conversion" is a measure of the quantity of starting material consumed in a specified reaction pathway. The term "high yield" as used herein refers to a useful molar percent yield in the range from about 60 percent to about 100 percent, and more preferably above about 75 percent. The term "selectivity" refers to and is calculated as a quantity of product of interest as a ratio of all products formed. The term "high selectivity" as used herein refers to a value above about 70 percent, and more preferably above about 85 percent.

Figure 2:
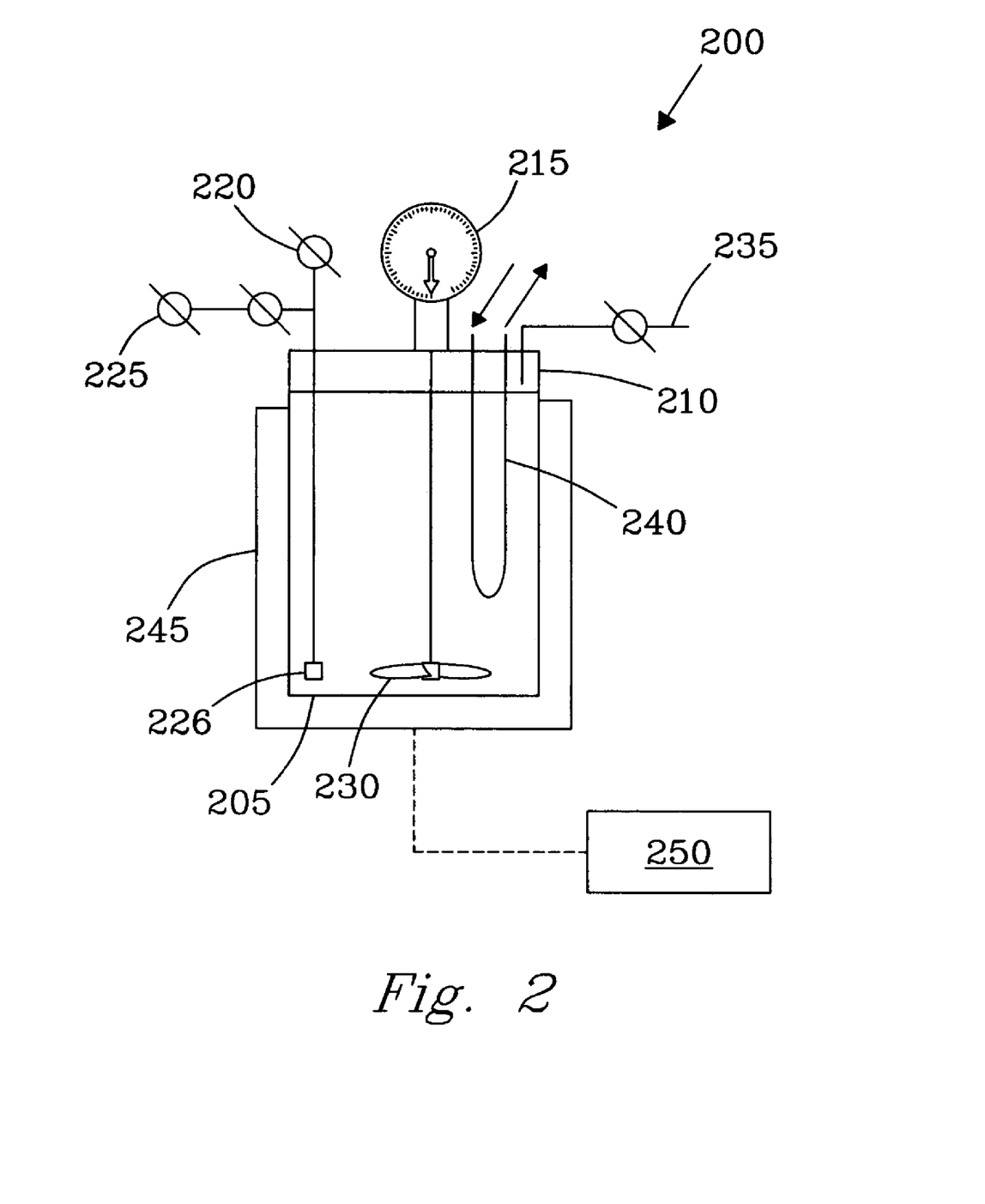
FIG. 2 illustrates a reaction vessel for practicing the process of the present invention.

FIG. 2 illustrates a typical reaction vessel (or reactor) 200 for practicing the process of the present invention. The reactor 200 (for example, a model 4565 Mini Reactor from Parr Instrument Co., Moline, Ill.) comprises a 100 mL high-pressure cylinder 205 and a cap assembly 210 made preferably of stainless steel or Hasteloy® or another high-refractory metal for operating temperatures up to about 350° C. The cap assembly 210 further comprises a pressure gauge 215, a gas inlet valve 220, a dip tube 225 for sampling, a magnetic stirring mechanism 230 for mixing vessel contents, a venting assembly 235, and a water cooling loop 240 for controlling temperature of the reactor vessel and contents.

The reactor cylinder and contents are sealed using two C-shaped capping rings (not shown) that mount over protruding edges machined into the cylinder 205 and cap assembly 210, respectively, and are secured in place by three capping screws located in each capping ring. The vessel cylinder inserts into a heater core 245 that heats the vessel contents. The assembled reactor vessel is secured into a supporting rack (not shown) providing stability at stirring speeds up to 1700 rpm. The vessel is further interfaced to a programmable pressure and temperature controller 250 (for example, a 4843 controller from Parr Instrument Co., Moline, Ill.).

Catalysts, solvents, and reagents may be added to the reactor vessel 205 prior to assembly. For example, the catalyst is preferably introduced to the reactor in a pre-reduced powder form prior to adding starting materials, but may be reduced in situ or in the vessel prior to adding other reagents. A filter 226 at the base of the dip tube 225 prevents powdered catalyst from entering the tube. The reactor is pressurized with nitrogen through the gas inlet port 220 to a pressure of from about 100 to about 500 psi and vented three times using the vent valve 235. The reactor is then pressurized with hydrogen to the desired starting pressure prior to heating. Samples are withdrawn by closing the gas inlet port and opening the dip tube and collecting fluid samples in a sample vial. Samples are allowed to cool to room temperature prior to analysis.

The reactor 200 may be alternately charged by loading solutions through the vent line 235. Solutions can be pumped in, or drawn in via gravity or vacuum. Because glutamic acid (GLU) has low solubility in water at 25° C. (8.64 g/L) [Merck Index, 10th ed., 1983, p. 641], or about 0.86 wt %, the solutions must be heated depending on the desired concentration for the starting materials. For example, at 50° C., GLU solubility increases to about 2.1 wt %; at 100° C. solubility increases still further to about 14 wt %. Alternatively, the solid may be added directly to the reactor vessel prior to heating or as the salt of the acid.

Figure 3A:
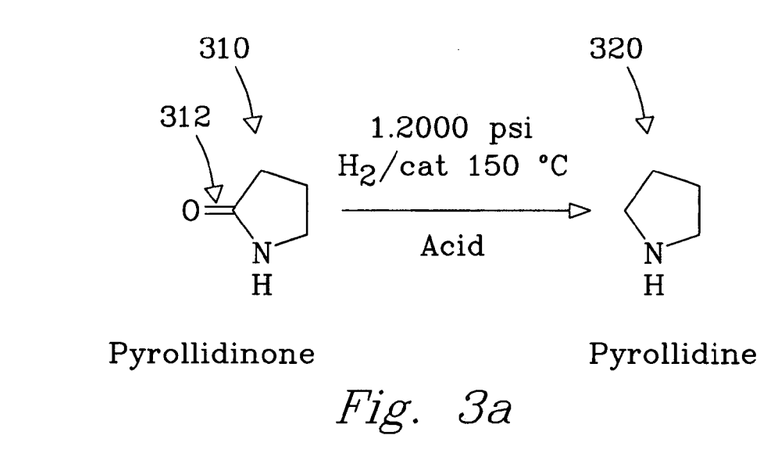
FIG. 3a illustrates a general reaction scheme for conversion of a pyrrolidinone to a pyrrolidine, according to an embodiment of the present invention.
Figure 3B:
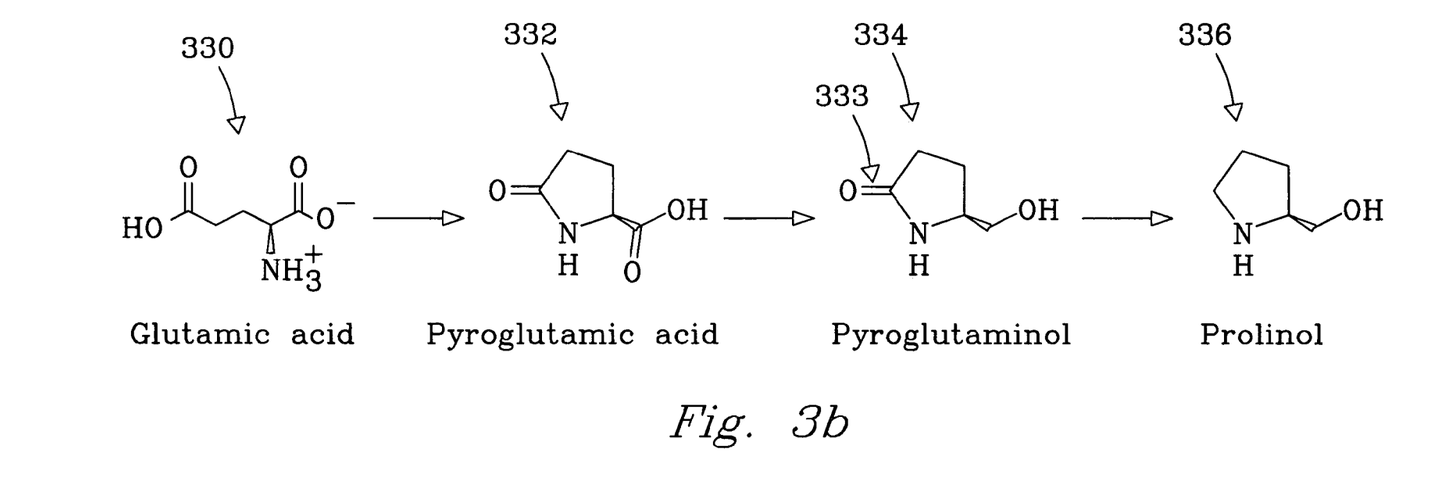
FIG. 3b illustrates a typical reaction scheme for conversion of glutamic acid, a representative amino acid, to prolinol (pyrrolidin-2-yl-methanol or PRO), according to an embodiment of the present invention.

The conversion of starting materials under acid-promoted hydrogenation conditions will now be described according to a process of the present invention. FIG. 3a illustrates a first generalized reaction scheme for conversion of pyrollidinones 310 to form pyrollidines 320, a desirable class of end-product compounds. As shown in the figure, the lactam carbonyl of the pyrrolidinone (i.e., carbonyl of the cyclic amide) 312 is selectively reduced. Reduction is effected in the presence of a reduction catalyst, a hydrogen partial pressure of up to about 3000 psi, and a preferred temperature of up to about 200° C. with a temperature of approximately 150° C. being more preferred, all in the presence of an acidic medium whereby the acid-promoted hydrogenation reaction occurs. FIG. 3b illustrates a second complete reaction pathway for conversion of a GLU 330 starting material, a representative amino acid, under acid-promoted hydrogenation conditions yielding a desirable pyrollidine end product, e.g., prolinol 336 (PRO). The starting material is first cyclized to yield pyroglutamic acid (PGA), a pyrrolidinone 332 (or cyclic amide). The acidic functional groups of the pyrrolidinone are converted under continued acid-promoted reduction conditions to form the alcohol, i.e., pyroglutaminol 334 (PGOL) or 5-HMP. A reaction step in the conversion of the pyrrolidinone 334 to a final pyrrolidine 336 product comprises reducing the lactam carbonyl 333 functional group ultimately yielding PRO 336. However, the reaction may be run under conditions that favor formation of either PGOL 334 or PRO 336. For example, in the presence of acid (e.g., $H_3PO_4$ or other mineral acid), conversion of the starting material is nearly 100 percent, with a molar ratio of PGOL to PRO formed being as high as 1 to 98. Under conditions in which no acid is added, PGOL is favored with a molar ratio of about 6 to 1 (PGOL: PRO).

Reaction (e.g., cyclization) results observed for conversion of glutamic acid and pyroglutamic acid were surprising under the acidic or low pH and dilute reagent conditions used, conditions normally favoring ring-opening, not cyclization. While cyclization can be done thermally, the rate for cyclization appears to be surprisingly enhanced in the presence of a hydrogenation catalyst, e.g., a transition metal on a carbon support.

The term "hydrogenation catalyst" as used herein refers to a reduction catalyst. Preferred catalysts include, but are not limited to, ruthenium (Ru), rhenium (Re), rhodium (Rh), platinum (Pt), palladium (Pd), copper (Cu), nickel (Ni), cobalt (Co), molybdenum (Mo), copper chromite, including various oxides and Raney forms thereof. Supports may include carbon (C), niobium (Nb), titania ($TiO_2$), zirconia ($ZrO_2$), silica ($SiO_2$), tin (Sn), alumina ($Al_2O_3$) or mixtures thereof.

Concentrations for the starting materials are ideally and preferably at the limit of solubility in the reaction solvent. For example, GLU concentration in the starting solvent is in the range of from about 1 to about 30 wt % in $H_2O$. More preferably, the starting concentration of GLU in the reaction solvent is in the range from 10 to about 30 wt %. For pyroglutamic acid (PGA), solubility is much greater in the reaction solvent, preferably in the range from 1% to about 70 wt %, with a range from about 10–50 wt % being more preferred, and from 10–30 wt % being most preferred. Solvent choices are myriad including alcohols such as methanol and ethanol, water, carbon dioxide, and non-protio solvents including, but not limited to, cyclohexane, alkanes, ethers, or combinations thereof. Solvents are selected based on the desired end products. Preferred solvents include water, methanol, and mixtures thereof, but are not limited thereto.

The formation of the pyrrolidine class of compounds is significant as cyclization reactions forming pyrrolidinone are representative and illustrative of conversion and formation of many like classes of useful compounds. Formation of pyrrolidines extends the types of products available from cyclization.

Various starting materials comprising various inherent functional groups may be used. For example, cyclization reactions may involve starting materials comprising R-group functionalities where R is selected from hydrogen (e.g., —H), as well as alkyl and aryl groups having carbon numbers in the range from about 1 to about 20, and moieties comprising non-reducing heteroatoms including, but not limited to, O (e.g., as in carbamate formation), and N (e.g., as in urea formation).

It may be undesirable to convert certain amino acid moieties under conditions of low pH as taught in the art. For example, processes of the present invention involving reactions such as cyclization are viewed as being extremely useful for selective conversion of starting materials whereby ringed compounds of varying size are formed. Addition of acid is not required and may promote unexpected or undesirable results. In particular, reducing a carboxylic acid functional group on a substituted lactam does not require use of acid. Addition of acid promotes reduction of the lactam carbonyl leading to a cyclic amine.

As a starting material, aspartic acid is expected to yield an intermediate or end product containing a 4-member ring. GLU yields compounds having a 5-member ring following cyclization. Lysine is expected to yield compounds containing a 7-member ring following cyclization. Ornithine, another similar compound, is also cyclizable. Further, additional and various R-functional groups including, but not limited to, —H, —$CH_2OH$, —COOH, and —$NH_2$ may be added to the cyclized N-reaction products thereby yielding a host of additional and desirable substituted intermediate and end-use products.

In short, the conversion process detailed for GLU and PGA is equally applicable to other amino acids moieties and related compounds including, but not limited to, lysine, aspartic acid, arginine, asparagine, glutamine, ornithine, and substitution products thereof. All conversion products as would be envisioned by the person of ordinary skill in view of the reaction processes of the present invention are hereby incorporated.

Choice of reaction temperature has proven to be important to the process yields, with elevated temperatures being the most useful. For example, reaction temperatures in the range from 30–200° C. are preferred, with a temperature in the range from 125–150° C. being more preferred. Further, a reducing atmosphere with a $H_2$ partial pressure in the range from about 15 psi to about 3000 psi. For reactions of the present invention involving an acidic medium, a pH of less than or equal to 3 is preferred.

Suitable acids include mineral acids such as hydrochloric (HCl) and sulfuric acid ($H_2SO_4$), although phosphoric acid ($H_3PO_4$) is preferred. Other choices for acids include carbon dioxide, carboxylic acids, amino acids, and solid acids, including but not limited to, acidic resins, acid zeolites, and acidic clays. Acidic resins include perfluorinated polymers or copolymers of tetrafluoroethylene and perfluoro-3,6-dioxa-4-methyl-7-octenesulfonyl fluoride, sold commercially under the tradename Nafion® resins (E.I. du Pont de Nemours and Company, 1007 Market Street, Wilmington, Del.). Other workable acid resins include the carboxylated polystyrenes and sulfonated polystyrenes, sold commercially under the tradenames Dowex® (Dow Company, 2030 Dow Center, Midland, Mich.) and Amberlyst® (Rohn and Haas, 100 Independence Mall West, Philadelphia, Pa.). Pyroglutamic acid (PGA) as a conversion product is also a suitable acid as it can catalyze reactions when no additional acid is added. However, at least one equivalent of PGA is generally required as the resulting product, prolinol (PRO), is a strong base that tends to form a salt with PGA. Such salts are unreactive toward metal catalyzed hydrogenation reactions, preventing high conversion of PGA to PGOL. For example, the salt is unreactive toward primary reduction (carboxylic acid to alcohol) or secondary reduction (lactam to imine). Thus to the extent that PGOL is formed, an equimolar amount of PGA is neutralized and does not react making full conversion unlikely.

Under certain conditions, acid-promoted reduction of PGOL to PRO may be undesirable. For example, if the intermediate PGOL is the desired end product, it may be favorable to arrest the reaction process at the formation of the intermediate moiety or alternatively conduct the reaction under different conditions vastly improving the specific product yield. In the absence of acid, as noted previously, PGOL can be favored in a molar ratio of about 6:1 (PGOL: PRO). Processes that achieve even higher selectivities are described hereinafter.

Figure 4A:
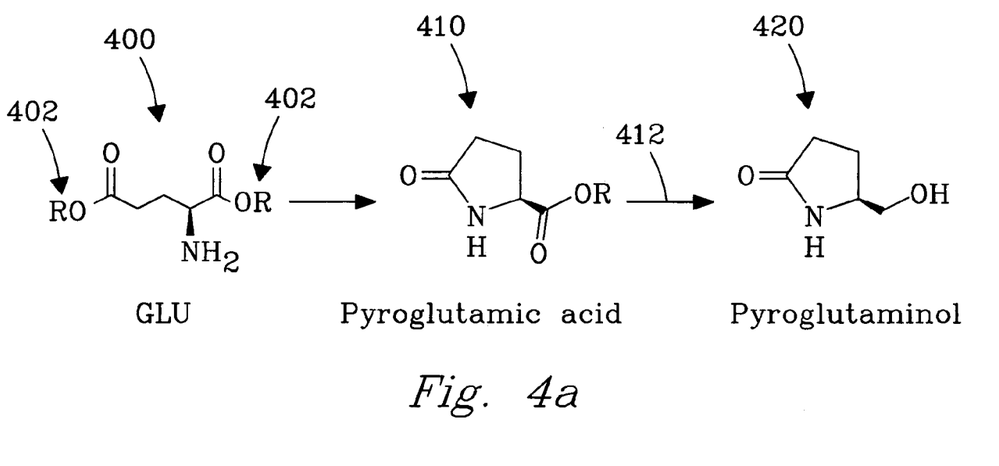
FIG. 4a illustrates a first reaction scheme for conversion of an esterified amino acid via an acid-promoted hydrogenation reaction to yield pyroglutaminol (5-hydroxymethyl-2-pyrrolidinone or 5-HMP), according to a further embodiment of the present invention.

The conversion of starting materials to pyrollidinones under non-acid promoted conditions at higher yields will now be described, according to a further embodiment of the present invention. As illustrated in FIG. 4a, the process generally comprises: a) providing a starting material, GLU and PGA being representative but not exclusive; b) esterifying the acid functional groups 402 of the starting material using R-functional compounds yielding an esterified precursor material 400. Esterification is done using methodologies known in the art. R-functional group compounds may be selected from alkylating agents, alcohols (e.g., R—OH) including, but not limited to, methanol, ethanol, and prolinol, alkyl halides, olefins, alkyl compounds (e.g., R—CH$_3$), aryl compounds, and combinations thereof. Esterifying the starting material permits the reduction and conversion reactions to be done under neutral or near-neutral conditions, e.g., in the absence of acid, thereby avoiding additional acid-promoted reactions or unwanted salt formation; c) optionally reacting, e.g., cyclizing, the esterified product yielding an esterified pyrrolidinone 410, e.g., esterified PGA; d) reducing the pyrrolidinone 410 in the presence of a reduction catalyst 412 to yield a final pyrrolidinone 420, e.g., PGOL.

Higher product yields may be effected by esterifying the various reaction products. Preferred reaction conditions include: 1) presence of a reduction catalyst including metals such as palladium, platinum, copper, copper chromite, nickel, and cobalt, or alternatively ruthenium, and rhenium, 2) a solvent for preparing the ester including, but not limited to methanol, ethanol, prolinol (product), non-protio solvents such as cyclohexane or other alkanes, and ethers, 3) a reaction temperature preferably in the range from about 10° C. to about 200° C., more preferably in the range from about 50° C. to about 180° C., and most preferably in the range from about 75° C. to 150° C., and 4) a hydrogen partial pressure preferably in the range from about 15 psi to about 3000 psi.

Significance of the instant embodiment is the predicted improvement in the yield of PGOL and its derivatives under non-acid-promoted or neutral pH conditions due to the high conversion of the starting material, i.e., GLU or PGA. Yields are selectively optimized for a desired product, e.g., PGOL.

Alternatively, in the absence of esterification, one may maintain the reactor medium at a controlled pH to achieve the desired conversion product. For example, buffering of the reactor medium containing a starting material such as GLU may be considered in order to maintain neutral pH. However, buffering of GLU is generally not ideal in this situation since the starting material must be in the acid form for reduction to occur.

Figure 4B:
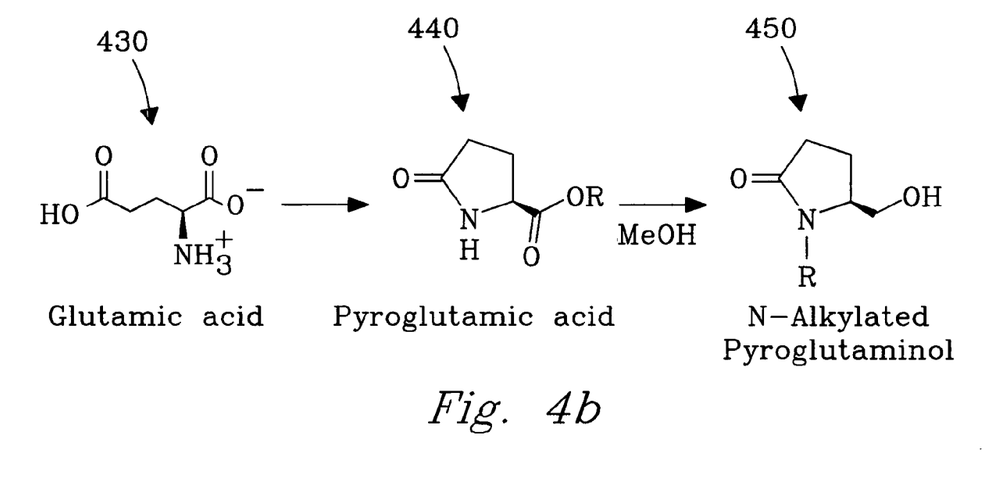
FIG. 4b illustrates an alternate reaction scheme for conversion of an amino acid starting material to yield N-alkylated substituted pyrrolidinones, including N-alkylated pyroglutaminol, according to a further embodiment of the present invention.

In another process of the present embodiment illustrated in FIG. 4b, N-substituted pyrrolidinones may be selectively produced, e.g., 5-hydroxy-1-methyl-2-pyrrolidinone, a potential high-value solvent. As shown in FIG. 4b, for example, following cyclization forming the pyrollidinone 440, N-substitution may be effected by addition of alcohol to the reactor with optional removal of water, resulting in conversion to N-alkylated pyrrolidinone 450. For example, conversion of PGA 440 to N-alkylated PGOL 450 may be achieved. Water may be actively removed by standard techniques known in the art including use of a drying agent or removal as an azeotrope. In a reactor solvent comprised entirely of alcohol (e.g., methanol), substitution of the pyrrolidinones 440 and 440 (or 410 and 420) occurs directly yielding the N-substituted (e.g., alkylated) pyrrolidinone 450.

In general, N-substituted products may be produced using compounds selected from alkylating agents, alcohols, alkyl halides, olefins, carbonates, sulfates, and sulfonates yielding functionalities including, but not limited to, —H, —CH$_3$, —OH, —C=O, —COOH, R—CH$_3$, R—COOH, -alkyl, -aryl, and -lactam carbonyl.

In FIG. 4b, a non-esterified starting material 430 may be converted from the zwitterionic form of the material. For example, GLU 430 as a zwitterion is cyclized thermally forming the pyrrolidinone 440, e.g., PGA. Pyrrolidinone 440 is subsequently converted to an N-substituted pyrrolidinone 450 by reduction in the presence of a reduction catalyst and an alkylating agent (e.g., methanol) yielding the N-alkylated PGOL. R-functional group compounds for substitution may be selected as envisioned by the person of ordinary skill in the art.

In general, preferred conversion of a starting material yielding N-substitution products comprises the steps a) providing a starting material 430 in a solvent at controlled pH, b) esterifying the starting material forming an esterified precursor material (e.g., the ester of GLU 400), c) optionally reacting (e.g., cyclizing) the esterified precursor material yielding at least one esterified pyrrolidinone or lactam, and d) reducing at least one esterified functional group of the precursor material in the presence of a reduction catalyst yielding at least one product at high yield, and d) further reacting with an R-functional group compound as discussed herein yields at least one final N-substituted product at high yield, e.g., N-alkylated PGOL 450.

Figures 5A, 5B:
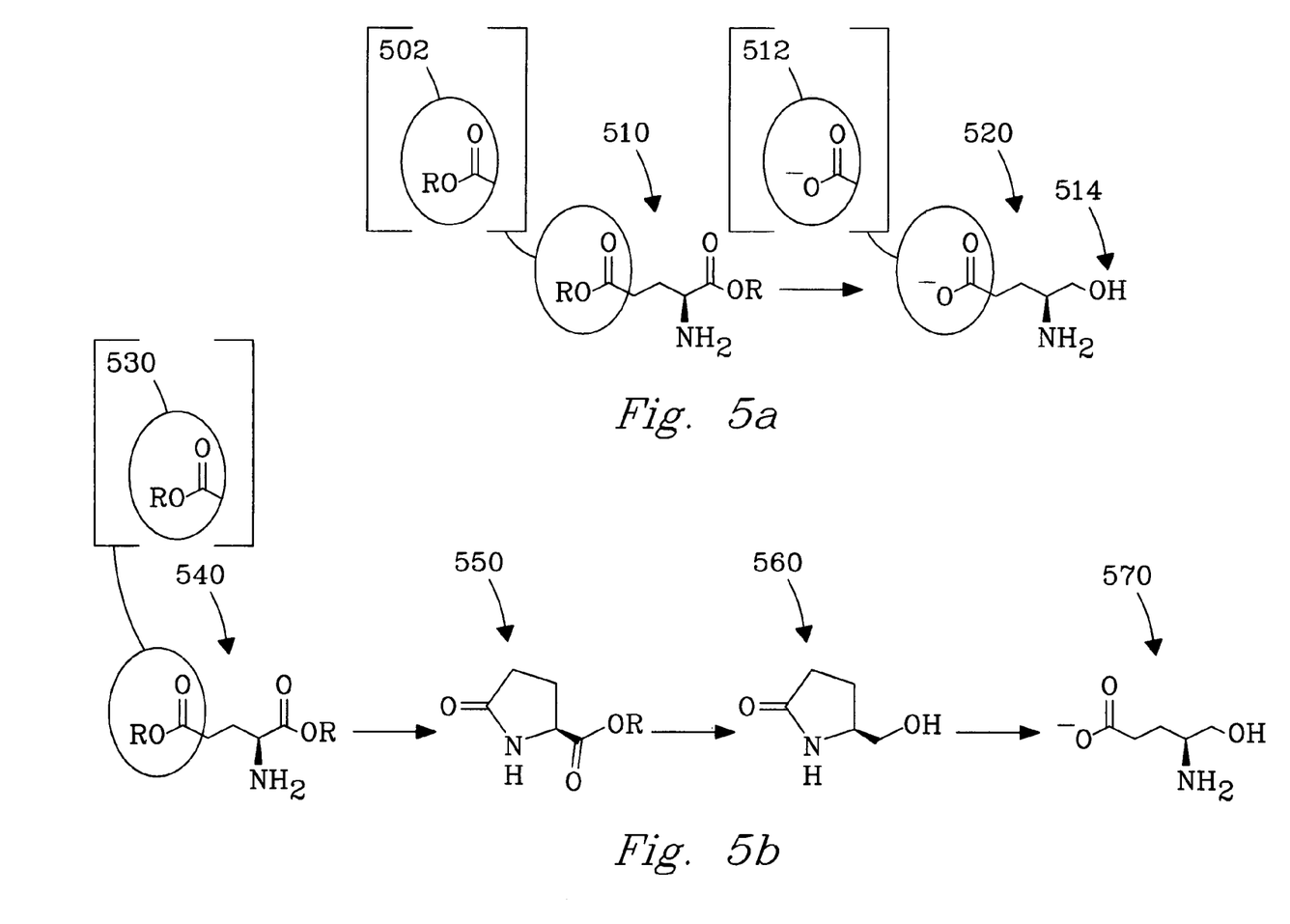
FIG. 5a illustrates a first typical reaction scheme for protection and selective conversion of an amino acid starting material comprising various functional groups to 4-amino-5-ol-pentanoic acid according to an additional embodiment of the present invention.
FIG. 5b illustrates a second typical reaction scheme involving glutamic acid for increasing the yield of a desired end product via esterification, cyclization, and subsequent ring opening according to an additional embodiment of the present invention.

FIG. 5a illustrates a general reaction process for conversion of a starting material using carbonyl activation arising from the alpha amino group according to an additional embodiment of the present invention. Acidic functional groups 502 of a starting material may be protected by esterifying the moieties yielding an esterified precursor material 510. Subsequent and selective reduction in the presence of a reduction catalyst yields the conversion product 520 comprising both a carboxylic acid functional group 512 and alcohol 514. If the reaction is performed in the presence of an R-functional group compound (R—OH) such as methanol, the acid functional group 512 will remain predominantly esterified. Esterification may be partial or complete. For example, if the reaction is performed in the presence of water, functional group 512 will likely be predominantly a free acid, or alternatively a salt or zwitterion. Temperatures are preferably below about 100° C. whereby esterification of the amino acid activates the alpha carbonyl selectively (i.e., α-amino activation effect) leading to the desired conversion product 520. Pressures of up to about 3000 psi are preferred, with pressures in the range from about 500 psi to 1500 psi being more preferred.

The esterified moieties may comprise R-functional groups selected from —R—CH$_3$, —CH$_3$, -lactam carbonyl, —C=O, —R—COOH, —COOH, —R—OH, -alkyl, -aryl, and —H, with carbon numbers for R in the range from about 1 to about 20. Where R=—H, the reaction medium is preferably controlled at a pH near the pI thereby maintaining the starting material in zwitterionic form, e.g., about 3.2–3.5 for GLU.

FIG. 5b illustrates a complete reaction scheme according to the instant embodiment for conversion of a representative starting material, e.g., GLU. In the starting material, carboxylic acid functional groups of glutamic acid, including the primary C-5 group 530 may be optionally protected initially by esterifying with an R-functional group compound yielding the esterified precursor material 540, where R is selected from -alkyl, and -aryl moieties with a carbon number in the range from about 1 to about 20. R may also be —H, although greater yields are expected using esterified precursors. Reacting (e.g., cyclizing) the precursor 540 yields an esterified pyrollidinone 550 (a cyclic amide) comprising a lactam carbonyl. Cyclization can be accomplished under thermal conditions in a solvent comprising water, alcohols, or mixtures thereof. Cyclization differentiates the lactam carbonyl preferentially over the carbonyl of the carboxylic acid. Thus, reduction in the presence of a reduction catalyst selectively yields the 5-ol product. Ring opening is effected under excess base conditions.

For GLU as a starting material, temperatures above 100° C. are preferred given that solubility of glutamic acid is 0.8 wt % in water at 25° C. Solubility of GLU increases under elevated temperatures reaching approximately 15 wt % at 100° C. Thus, GLU solutions must be kept warm or precipitation occurs. Cyclization of GLU can also be done in dilute solutions comprising the starting material in water thereby forming pyroglutamic acid (PGA). PGA may also be used as a starting material which is advantageous given its high water solubility. The person of ordinary skill in the art will recognize the potential for conversion of many like starting materials.

In FIG. 5b, pyrrolidinones 550 and 560 show an N-substitution comprising —H, but are not limited thereto. For example, R-group functionalities as previously described may be substituted. Continued reduction of the esterified pyrrolidinone 550 in the presence of a reduction catalyst results in selective removal of the R-functional ester yielding the -ol form of the pyrrolidinone, e.g., a pyroglutaminol (PGOL) 560 or other N-substituted pyrrolidinone products. The resulting pyrrolidinone comprises both a lactam carbonyl and a free alcohol, e.g., the 6-ol. Base-promoted ring opening yields a five-carbon moiety, e.g., 4-amino-5-ol-pentanoic acid 570, a desirable end product.

In general, selective reduction of one or more carboxylic acid groups of GLU represents a desirable conversion and transformation process for making novel five-carbon compounds, the selective conversion of GLU to 4-amino-5-ol-pentanoic acid being a notable example. Uses for the conversion products include potential applications as polymers, coatings, and adhesives. The reaction scheme illustrated in FIG. 5b involving esterification is anticipated to increase conversion product yields. For example, highest yields for reaction products during hydrogenation of GLU should be achieved by converting esterified intermediates as described herein.

One of many desirable conversion products of GLU is PGOL. As illustrated in FIG. 5b, conversion of PGOL to other useful end products comprises ring opening. Ring opening may be effected by adding base to the reactor. Further, in the presence of a base at elevated temperature esterified functionalities protecting the C-5 carboxylic acid group are also removed yielding the free PGOL. The base may be any suitable alkali metal hydroxide, alkaline earth metal hydroxide, basic amine, or other Brönsted or Lewis base. The amount of base can be catalytic or up to an equimolar amount. For example, one molar equivalent of base may be added to the reaction vessel and contents heated for approximately one hour at a temperature in the range from about 20° C. to 200° C., 150° C. being typical. Reactions may be effected in the same reactor vessel or alternatively in a separate reactor. Alternatively, temperatures can be significantly lower, e.g., in the range from 50° C. to 100° C. depending on desired reaction outcomes as discussed previously.

Lewis acids may also be employed to tie up the more acidic amino acid group leaving the less acidic carboxylic acid to be reduced. Preferred Lewis Acids include the chlorides, sulfates, oxides, nitrates, and acetates of tin (Sn) and zinc (Zn). One to two equivalents of the Lewis acid are added to the reaction mixture. Hydrogenation is done using the catalysts and conditions described herein. Conversion products form as salts allowing for improved selective reduction of the pendant acid, for example, at position C-5. Catalyst choices when converting ester forms of the starting materials are preferably selected from Pd, Pt, Ni, Cu, Co, including the oxides and Raney forms thereof. The Lewis acid complex is required to selectively chelate the amine-N and carbonyl (C=O) functional groups, leaving the C-5 or other pendant carboxylic acids available for reduction. Preferred reaction conditions include 1) a temperature in the range from about 50 to about 100° C., the lower temperature being preferred to prevent cyclization, 2) a partial hydrogen pressure of from about 15 psi to 2000 psi, and 3) addition of a Lewis acid at a concentration of from 1 to 2 molar equivalents if the solvent is alcohol or a concentration of from 1 to about 100 equivalents if the solvent is water.

Figure 6:
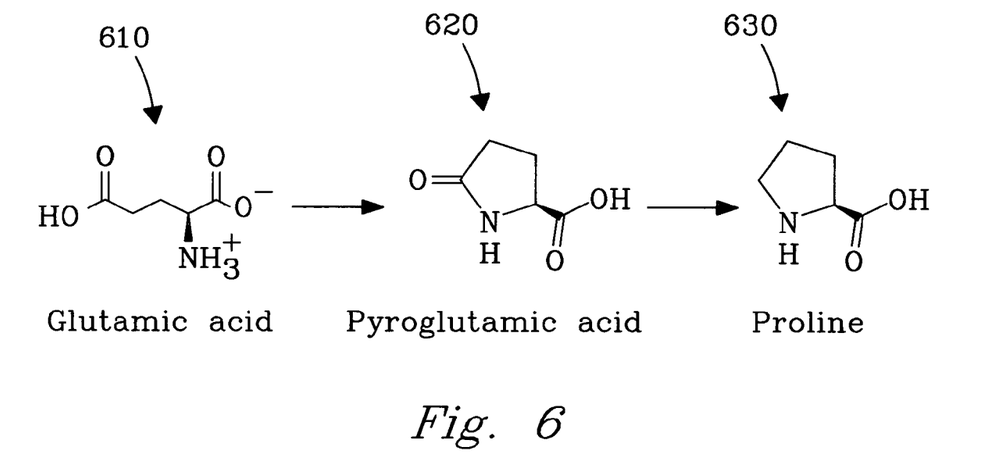
FIG. 6 illustrates a typical selective reduction of glutamic acid to yield proline according to a still further embodiment of the present invention.

FIG. 6 illustrates a process for selective conversion of an amino acid starting material 610 by selective deactivation to a desirable end product 630 according to a further embodiment of the present invention. Control over the reaction is maintained by selectively deactivating the pendant carboxylic acid functional group while selectively promoting the reduction of the lactam carbonyl functionality. For example, a representative amino acid, GLU 610 can be converted to PGA 620 as described previously, with a subsequent final conversion to proline 630. The process generally comprises: a) optionally reacting (e.g., cyclizing) the starting material 610 yielding a lactam, a cyclic amide comprising a lactam carbonyl, e.g., PGA 620, and b) deprotonating the pendant carboxylic acid of the lactam with a base or a Lewis acid allowing for selective reduction of the lactam in the presence of a reduction catalyst yielding PRO 630. Preferred reduction catalysts include palladium (Pd) and platinum (Pt) given the low propensity to reduce the carboxylic acid functional groups. However, other catalysts are also workable. For example, catalysts that tend to hydrogenate carboxylic acid groups, including Ru or Re, may be employed if weak bases are added to maintain the carboxylate form of the acid, i.e., the non-protonated form. Preferred weak bases include amines, cyclic amines, bisulfates, phosphates, phosphites, acetates, and the like. Lewis acids may also serve the same purpose. Strong bases should not be employed in excess as they lead to ring opening. Catalysts on carbon supports that have been treated to be basic are preferred. Such supports assist in desorbing the strong base proline thereby disfavoring further reduction.

When using a Re or Ru catalyst, Lewis acids are used in excess in the range from about 1 to about 100 equivalents.

With other catalysts, the Lewis acid can be employed in catalytic amounts. Thus, preferred catalysts follow in the order Pd, Pt, Rh, Cu, Mo, Co, and lastly Re or Ru.

Reaction temperature is preferably in the range from about 50° C. to about 200° C., with a temperature in the range from about 100° C. to about 150 ° C. being more preferable. A hydrogen pressure between about 1 to about 10 atm is also preferred. Reaction solvent preferably comprises water, alcohols, or mixtures thereof.

The following examples are intended to promote a further understanding of the present invention. Example 1 demonstrates the hydrogenation of PGA in the presence of an acid to produce PGOL. Examples 2–6 demonstrate hydrogenation reactions involving GLU, PGA, and PRO in the presence of acid. Example 7 demonstrates hydrogenation of PGA in the absence of acid. Examples 8–12 demonstrate conversion of PGOL to PRO in the absence of acid, by precious metal catalysis. Example 13 demonstrates conversion of PGOL to PRO is promoted by acid in the presence of precious metal catalysts resulting in hydrogenation and reduction of the lactam carbonyl occurs. Example 14 demonstrates that conversion of PGOL to form PRO is promoted by acid; in the absence of acid, conversion does not occur. Example 15 demonstrates base promoted ring opening of cyclic amino acids and/or lactams.

EXAMPLE 1

Experimental. A 100 mL reactor 200 was charged with 2 g of a 5% ruthenium-supported-on-carbon powder catalyst (ESCAT™-440, Engelhard Corp., Iselin, N.J.) and 100 mL of a water solution comprising 0.22M PGA (Sigma-Aldrich Corp., St. Louis, Mo.) further comprising 0.29M phosphoric acid diluted from the 85% reagent grade acid (Sigma-Aldrich Corp., St. Louis, Mo.). The catalyst came in pre-reduced form comprising 50% water by weight. The reactor 200 was charged with hydrogen to a pressure of 900 psi and heated to 150° C. Upon reaching the desired temperature the reactor pressure was adjusted to 2,000 psi $H_2$. The reaction was allowed to proceed four hours. Samples were taken throughout the run.

Results. The maximum yield of PGOL (47% molar yield) was reached at a conversion of 88% in approximately 1 hour. PGOL was converted to PRO upon further reaction. After 4 hours, conversion of the starting material was complete with approximate product yields of 10% PGOL and 90% PRO.

EXAMPLES 2–6

Experimental. Examples 2–6 followed the same procedure as in Example 1 with changes to either hydrogen pressure or concentration of the starting material. Results are summarized in Table 1 below.

TABLE 1

Conversion results for a starting material in an acidified medium.

| | Preparation | | | Reaction Conditions | | Run | Conversion Results | | |
|---|---|---|---|---|---|---|---|---|---|
| Example | Starting Material [0.22 M] | $H_3PO_4$ [M] | Catalyst | Temp (° C.) | $H_2$ (Psig) | Time (Hr) | Conversion (Mol %) | Selectivity PGOL | Selectivity PRO |
| 2 | PGA | 0.29 | 5% Ru/C | 150 | 2000 | 4 | 99.8 | 10 | 90 |
| 3 | PGA | 0.29 | 5% Ru/C | 150 | 1000 | 4 | 99.6 | 48 | 48 |
| 4 | GLU | 0.29 | 5% Ru/C | 150 | 2000 | 4 | 100 | 14 | 85 |
| 5 | PRO | 0.29 | 5% Ru/C | 150 | 1000 | 3.5 | 98 | nd | 98 |
| 6 | GLU | 0.29 | 5% Ru/C | 150 | 2000 | 4 | 98 | 1 | 98 |

Where GLU = Glutamic Acid; PGA = Pyroglutamic acid; PGOL = Pyroglutaminol; PRO = Prolinol (5 HMP); nd = not detected Results. In general, results showed high conversion of GLU and GLU conversion compounds (e.g., PGA) using precious metal catalysis in the absence of additional acid. Further, results in Table 1 show that in the acidic medium comprising a Ru catalyst, PRO was selectively generated. Generally, the reaction converting PGOL to PRO was slower than the conversion of PGA to PGOL. However, results show a high conversion of starting materials above about 90% and high selectivity for prolinol above about 80%.

EXAMPLE 7

Experimental. A 100 mL reactor 200 was charged with 2 g of a 5% ruthenium-supported-on-carbon powder catalyst (ESCAT™-440, Engelhard Corp., Iselin, N.J.) and 100 mL of a water solution comprising 0.22M PGA (Sigma-Aldrich Corp., St. Louis, Mo.). No acid was added to the reactor. The catalyst was added in pre-reduced form comprising 50% water by weight. The reactor 200 was charged with hydrogen to a pressure of 900 psi and heated to 150° C. Upon reaching the desired temperature the reactor pressure was adjusted to 2,000 psi $H_2$. The reaction was allowed to proceed four hours. Samples were taken throughout the run.

Results. The maximum yield of PGOL (63% yield, 76% selectivity) was reached at a conversion of 83% after 1 hour. The primary by-product was PRO. Further reaction time did not lead to a significant increase in either conversion or yield. In the absence of acid, formation of PRO yields a salt with PGA. As a salt, PGA does not hydrogenate. Thus, further conversion does not occur.

EXAMPLES 8–12

Experimental. The reaction 200 was charged as detailed in Example 7, i.e., no added acid, with selective changes to temperature, pressure, or reduction catalyst. Samples were taken throughout the run. Results are summarized in Table 2 below.

TABLE 2

Conversion results for a starting material in a non-acidified solution medium.

| | Preparation | | | Reaction Conditions | | | Conversion Results | | |
|---|---|---|---|---|---|---|---|---|---|
| Example | Starting Material [0.2 M] | $H_3PO_4$ [M] | Catalyst | Temp (° C.) | $H_2$ (Psig) | Run Time (Hr) | Conversion (Mol %) | Selectivity PGOL | Selectivity PRO |
| 8 | PGA | 0 | 5% Ru/C | 150 | 2000 | 4 | 84 | 74 | 25 |
| 9 | PGA | 0 | 5% Ru/C | 150 | 1000 | 4 | 91 | 85 | 14 |
| 10 | PGA | 0 | 5% Rh/C | 150 | 1000 | 2.5 | 11 | 54 | 32 |
| 11 | PGA | 0 | 10% Pt/C | 150 | 1000 | 2.5 | 12 | 51 | 49 |
| 12 | PGA | 0 | 10% Pd/C | 150 | 1000 | 2.5 | 15 | 39 | 36 |

PGA = Pyroglutamic acid; PGOL = Pyroglutaminol; PRO = Prolinol

Results. Results in Table 2 show the ruthenium catalyst to be a preferred for conversion of PGA as the free acid (i.e., non-esterified form), with only low to moderate results in the presence of other catalysts. Selectivity for PGOL decreases with decreases in temperature and pressure.

EXAMPLE 13

Experimental. A 100 mL reactor 200 was charged with 2 g of a 5% ruthenium-supported-on-carbon powder catalyst (ESCAT™-440, Engelhard Corp., Iselin, N.J.) and 100 mL of a water solution comprising 0.22M PGA (Sigma-Aldrich Corp., St. Louis, Mo.) further comprising 0.29M phosphoric acid diluted from the 85% reagent grade acid (Sigma-Aldrich Corp., St. Louis, Mo.). The catalyst came in pre-reduced form comprising 50% water by weight. The reactor was charged with hydrogen to a pressure of 200 psi and heated to 150° C. Upon reaching the desired temperature the reactor pressure was adjusted to 1,000 psi $H_2$. The reaction was allowed to proceed for 3.5 hours. Samples were taken throughout the run.

Results. At 1000 psi $H_2$, conversion of PGOL to PRO was 98% in 3.5 hours, demonstrating essentially complete conversion to a single product at high yield. Results demonstrate that conversion of PGBL to PRO (via hydrogenation of the lactam) is promoted by acid in the presence of precious metal catalysts.

EXAMPLE 14

Experimental. A 100 mL reactor 200 was charged with 2 g of a 5% ruthenium-supported-on-carbon powder catalyst (ESCAT™-440, Engelhard Corp., Iselin, N.J.) and 100 mL of a water solution comprising 0.22M pyroglutaminol. No acid was added to the reactor. The reactor was further charged with hydrogen to a pressure of 400 psi and heated to 150° C. Upon reaching the desired temperature, the reactor pressure was adjusted to 2,000 psi $H_2$. The reaction was allowed to proceed for 3.5 hours. Samples were taken throughout the run.

Results. At 2.5 hours, the major product identified by High-Performance Liquid Chromatography was the starting PGOL, with conversion at less than 5%. No PRO was detected. Results demonstrate conversion of PGOL to PRO is promoted by acid. In the absence of added acid, conversion does not occur.

EXAMPLE 15

Experimental. A 100 mL reactor 200 was charged with 2 g of a 5% ruthenium-supported-on-carbon powder catalyst (ESCAT™-440, Engelhard Corp., Iselin, N.J.) and 100 mL of a water solution comprising 0.22M PGA and 0.44M sodium hydroxide. The reactor was charged with hydrogen to a pressure of 200 psi and heated to 150° C. Upon reaching the desired temperature the reactor pressure was adjusted to 2,000 psi $H_2$. The reaction was allowed to proceed for two hours. Samples were taken throughout the run.

Results. Results show that approximately 80% of the PGA was converted to glutamate after only 30 minutes at temperature. $^{13}C$ NMR analysis showed no other products formed. Results demonstrate that ring opening can be accomplished by heating in the presence of base. Use of catalysts may not be required for the ring opening reaction. In general, it is expected that strong bases will not promote reduction of lactams.

While the preferred embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

We claim:

1. A process for converting a starting material to a conversion products at high yield, comprising the steps:
   (a) providing said starting material in a solvent comprising acid, wherein said starting material comprises an amide or said starting material dehydrates to form an amide;
   (b) optionally dehydrating said starting material thereby yielding an amide; and,
   (c) reducing an amide carbonyl of said amide in the presence of a reduction catalyst thereby yielding at least one conversion product absent said amide carbonyl at high yield.

2. The process of claim 1, wherein said starting material is selected from the group consisting of amino acids, amides, lactams, pyrrolidinones, or combinations thereof.

3. The process of claim 1, wherein said starting material is selected from the group consisting of glutamic acid, pyrrolidinones, 2-pyrrolidinone, N-methyl pyrrolidinone, pyroglutamic acid, pyroglutaminol, or combinations thereof.

4. The process of claim 2, wherein said starting material comprises a carbon number in the range from about 1 to about 20.

5. The process of claim 2, wherein said amino acids are selected from the group consisting of lysine, aspartic acid, asparagine, glutamine, glutamic acid, arginine, pyroglutamic acid, ornithine, and combinations thereof.

6. The process of claim 2, wherein said amides are cyclic amides.

7. The process of claim 1, wherein said reducing comprises selective reduction of a lactam carbonyl of said amide.

8. The process of claim 1, wherein said at least one conversion product is selected from the group consisting of amines, cyclic amines, alcohols, and combinations thereof.

9. The process of claim 1, wherein said at least one conversion product contains a ring having a carbon number in the range from about 4 to about 7.

10. The process of claim 1, wherein said at least one conversion product is prolinol.

11. The process of claim 1, wherein said solvent is selected from the group consisting of alcohols, methanol, ethanol, water, carbon dioxide, non-protio solvents, alkanes, cyclohexane, ethers, and combinations thereof.

12. The process of claim 1, wherein the reducing comprises heating said starting material at a temperature in the range from about 100° C. to about 200° C. under a hydrogen pressure in the range from about 15 psi to about 3000 psi.

13. The process of claim 1, wherein said acid is selected from HCl, $H_2SO_4$, $H_3PO_4$, carbon dioxide, amino acids, carboxylic acids, solid acids, and combinations thereof.

14. The process of claim 13, wherein said solid acids are selected from acidic resins, acidic zeolites, acidic clays, and combinations thereof.

15. The process of claim 14, wherein said acidic resins are selected from perfluorinated polymers and copolymers comprising tetrafluoroethylene, perfluoro-3,6-dioxa-4-methyl-7-octenesulfonyl fluoride, carboxylated polystyrenes, sulfonated polystyrenes, and combinations thereof.

16. The process of claim 1, wherein the acid has a molar ratio to starting material of less than or equal to about 1.2.

17. The process of claim 1, wherein said reduction catalyst is selected from Ru, Re, Pd, Pt, Cu, Co, Mo, Ni, Rh, and combinations thereof.

18. The process of claim 17, wherein said catalyst comprises a solid support.

19. The process of claim 17, wherein said solid support is a carbon support.

20. The process of claim 17, wherein said catalyst is unsupported.

21. The process of claim 1, further comprising a reaction time of up to about 8 hours.

22. The process of claim 1, wherein the yield is up to about 100 percent.

23. The process of claim 1, wherein the yield is at least about 80 percent.

* * * * *

UNITED STATES PATENT AND TRADEMARK OFFICE
CERTIFICATE OF CORRECTION

| | | |
|---|---|---|
| PATENT NO. | : 7,049,446 B2 | Page 1 of 1 |
| APPLICATION NO. | : 10/841687 | |
| DATED | : May 30, 2006 | |
| INVENTOR(S) | : Johnathan E. Holladay | |

It is certified that error appears in the above-identified patent and that said Letters Patent is hereby corrected as shown below:

On Title Page, Col. 1 item (75) Inventor: please replace Johnathan E. Holladay, with –Johnathan E. Holladay--.

Signed and Sealed this

Fifteenth Day of August, 2006

JON W. DUDAS
*Director of the United States Patent and Trademark Office*

UNITED STATES PATENT AND TRADEMARK OFFICE
CERTIFICATE OF CORRECTION

PATENT NO.       : 7,049,446 B2  
APPLICATION NO.  : 10/841687  
DATED            : May 23, 2006  
INVENTOR(S)      : Johnathan E. Holladay

It is certified that error appears in the above-identified patent and that said Letters Patent is hereby corrected as shown below:

On Title Page, Col. 1 item (75) Inventor: please replace Johnathan E. Holladay, with --Johnathan E. Holladay--.

This certificate supersedes Certificate of Correction issued August 15, 2006.

Signed and Sealed this

Nineteenth Day of September, 2006

JON W. DUDAS  
*Director of the United States Patent and Trademark Office*